(12) United States Patent
Lee

(10) Patent No.: US 9,474,765 B2
(45) Date of Patent: Oct. 25, 2016

(54) COMPOSITION FOR LIPOLYSIS, CONTAINING PHOSPHATIDYLCHOLINE, AND PREPARATION METHOD THEREFOR

(71) Applicant: AMI Pharm Co., Ltd., Seoul (KR)

(72) Inventor: Ki Teak Lee, Seongnam-si (KR)

(73) Assignee: AMI Pharm Co., Ltd., Seoul (KR)

( * ) Notice: Subject to any disclaimer, the term of this patent is extended or adjusted under 35 U.S.C. 154(b) by 0 days.

(21) Appl. No.: 14/936,531

(22) Filed: Nov. 9, 2015

(65) Prior Publication Data

US 2016/0058780 A1    Mar. 3, 2016

Related U.S. Application Data

(63) Continuation of application No. PCT/KR2014/003728, filed on Apr. 28, 2014.

(30) Foreign Application Priority Data

May 10, 2013 (KR) ........................ 10-2013-0053117

(51) Int. Cl.
*A61K 31/685* (2006.01)
*A61K 9/00* (2006.01)
*A61K 47/10* (2006.01)
*A61K 47/44* (2006.01)

(52) U.S. Cl.
CPC ........... *A61K 31/685* (2013.01); *A61K 9/0019* (2013.01); *A61K 47/10* (2013.01); *A61K 47/44* (2013.01)

(58) Field of Classification Search
CPC .................................................. A61K 31/685
USPC ......................................................... 514/78
See application file for complete search history.

(56) References Cited

U.S. PATENT DOCUMENTS

2005/0267080 A1   12/2005   Kolodney et al.
2012/0149664 A1    6/2012   Yamasaki et al.

FOREIGN PATENT DOCUMENTS

KR   10-2004-0108567   12/2004
KR   10-2007-0110351   11/2007

OTHER PUBLICATIONS

Rotunda et al., "Mesotherapy and Phosphatidylcholine Injections:Historical Clarification and Review", Durmatologic Surgery, Apr. 2006, p. 465-480, vol. 32 No. 4.
Rotunda et al., "Detergent Effects of Sodium Deoxycholate Are a Major Feature of an Injectable Phosphatidylcholine Formulation Used for Localized Fat Dissolution", Durmatologic Surgery, Jul. 2004, p. 1001-1008, vol. 30 No. 7.
International Search Report issued on Aug. 27, 2014, in International Patent Application No. PCT/KR2014/003728.
Machine Translation of Korean Patent Application Publication No. 10-2004-0108567 to Choi et al., issued on Dec. 24, 2004.

*Primary Examiner* — Taofiq A Solola
(74) *Attorney, Agent, or Firm* — H.C. Park & Associates, PLC

(57) ABSTRACT

A composition for inducing lipolysis includes phosphatidylcholine and a preparation method therefor. More particularly, the composition for inducing lipolysis may include 2-12% (w/v) of phosphatidylcholine, 5-12% (w/v) of an oily solvent, and a balance of water; and a preparation method thereof. The composition may include phosphatidylcholine, an oily solvent, and water to induce lipolysis without causing such adverse side effects as edema, erythema, tissue necrosis, and inflammation.

4 Claims, 9 Drawing Sheets

COMPOSITION FOR LIPOLYSIS, CONTAINING PHOSPHATIDYLCHOLINE, AND PREPARATION METHOD THEREFOR

CROSS-REFERENCE TO RELATED APPLICATIONS

This application is a continuation of International Patent Application No. PCT/KR2014/003728, filed on Apr. 28, 2014, which claims priority from and the benefit of Korean Patent Application No. 10-2013-0053117, filed on May 10, 2013, both of which are hereby incorporated by reference for all purposes as if fully set forth herein.

BACKGROUND

1. Field

Exemplary embodiments relate to a composition for inducing lipolysis comprising phosphatidylcholine and a preparation method thereof. More particularly, exemplary embodiments relate to a composition for lipolysis comprising 2-12% (w/v) of phosphatidylcholine, 5-12% (w/v) of an oily solvent, and a balance of water wherein % (w/v) is based on the total composition.

2. Discussion of the Background

Phosphatidylcholines are a class of phospholipids that contain choline as a head group. They are widely present in animals, plants, yeasts and fungi, and are also known as lecithin. They are the membrane phospholipids of mammals and are found mainly in brains, nerves, blood cells, egg yolks and the like. In plants, phosphatidylcholines are found in soybeans, sunflower seeds, wheat germs and the like. Phosphatidylcholines generally contain saturated fatty acid at position 1 of glycerol and unsaturated fatty acid at position 2 of glycerol.

There exist around 20 billion adipocytes in the body of a mammalian animal including humans which function to store or release energy. There are complex mechanisms of regulating energy storage and release in the adipocytes. When a supply for energy is much larger than its demand, energy is stored as a form of triglycerides which are in turn decomposed into glycerol and free fatty acids for use in case of energy depletion. However, adipocytes are greatly accumulated in people of the modern time who over-consume energies and lack physical activities. Especially, spending a large amount time in a sitting position causes an inclination of a localized accumulation of fats in a specific area of body such as the abdomen or the lower limbs. Hence, there is an urgent need for a substance which is excellent in inducing lipolysis, particularly, inducing a localized lipolysis.

Polyene phosphatidylcholine, which have long been used as an agent for treating liver disorders and fat embolism, is also utilized as a main component in injectable formulations for inducing a localized lipolysis for cosmetic and plastic purposes. However, it has been reported that the effect of the injectable formulation in inducing a localized lipolysis was caused by sodium deoxycholate used as a solubilizer which induces inflammation in adipose tissues and leads to the death of adipocytes, not by polyene phosphatidylcholine used as a main component (See Rotunda A M, Suzuki H, Moy R L, Kolodney M., Detergent effects of sodium deoxycholate are a major feature of an injectable phophatidylcholine formulation used for localized fat dissolution. Dermatol Surg 30(7):1001-8(2004)). However, the local administration of sodium deoxycholate has received serious complaints from both patients and physicians since it damages musculoskeletal cells as well as adipocytes, along with such adverse side-effects as erythema, edema, bruise, hematoma and pain. Further, a formulation containing a large amount, i.e. 93% or more, of polyene phosphatidylcholine is a wax-like phase solid material which per se is insoluble in water. Hence, sodium deoxycholate was added as a solubilizer to prepare an intravenously injectable formulation. However, due to the report regarding sodium deoxycholate's side-effects upon its local administration, there is an urgent need for the development of a phosphatidylcholine-containing, water-soluble injectable formulation which contains no sodium deoxycholate with the reduction of its side-effects and possesses a similar effectiveness to the above-mentioned injectable formulation.

The above information disclosed in this Background section is only for enhancement of understanding of the background of the inventive concept, and, therefore, it may contain information that does not form the prior art that is already known in this country to a person of ordinary skill in the art.

SUMMARY

Exemplary embodiments provide a composition which is excellent in inducing a localized lipolysis without causing such adverse side effects as edema, erythema, tissue necrosis and inflammation.

Additional aspects will be set forth in the detailed description which follows, and, in part, will be apparent from the disclosure, or may be learned by practice of the inventive concept.

According to exemplary embodiments, the present invention is to provide a composition for inducing lipolysis comprising 1-15% (w/v) of phosphatidylcholine, 1-30% (w/v) of an oily solvent, and a balance of water. The said % (w/v) is based on the total composition.

According to exemplary embodiments, the present invention is to provide a method for preparing a composition for inducing lipolysis, the method comprising the steps of:

(a) stirring 1-15% (w/v) of phosphatidylcholine at a temperature of 60-80° C. for ½ to 2 hours;

(b) mixing 1-30% (w/v) of an oily solvent, which is heated to 60-80° C., with the stirred mixture of step (a); and (c) adding water until a pre-determined total volume is reached and stirring.

The said % (w/v) is based on the total composition.

According to exemplary embodiments, the present invention is to provide a method for inducing a localized lipolysis, the method comprising administering an effective amount of the composition for inducing lipolysis according to the present invention to a subject in need thereof.

The foregoing general description and the following detailed description are exemplary and explanatory and are intended to provide further explanation of the claimed subject matter.

BRIEF DESCRIPTION OF THE DRAWINGS

The accompanying drawings, which are included to provide a further understanding of the inventive concept, and are incorporated in and constitute a part of this specification, illustrate exemplary embodiments of the inventive concept, and, together with the description, serve to explain principles of the inventive concept.

DETAILED DESCRIPTION OF THE ILLUSTRATED EMBODIMENTS

Figure 1:
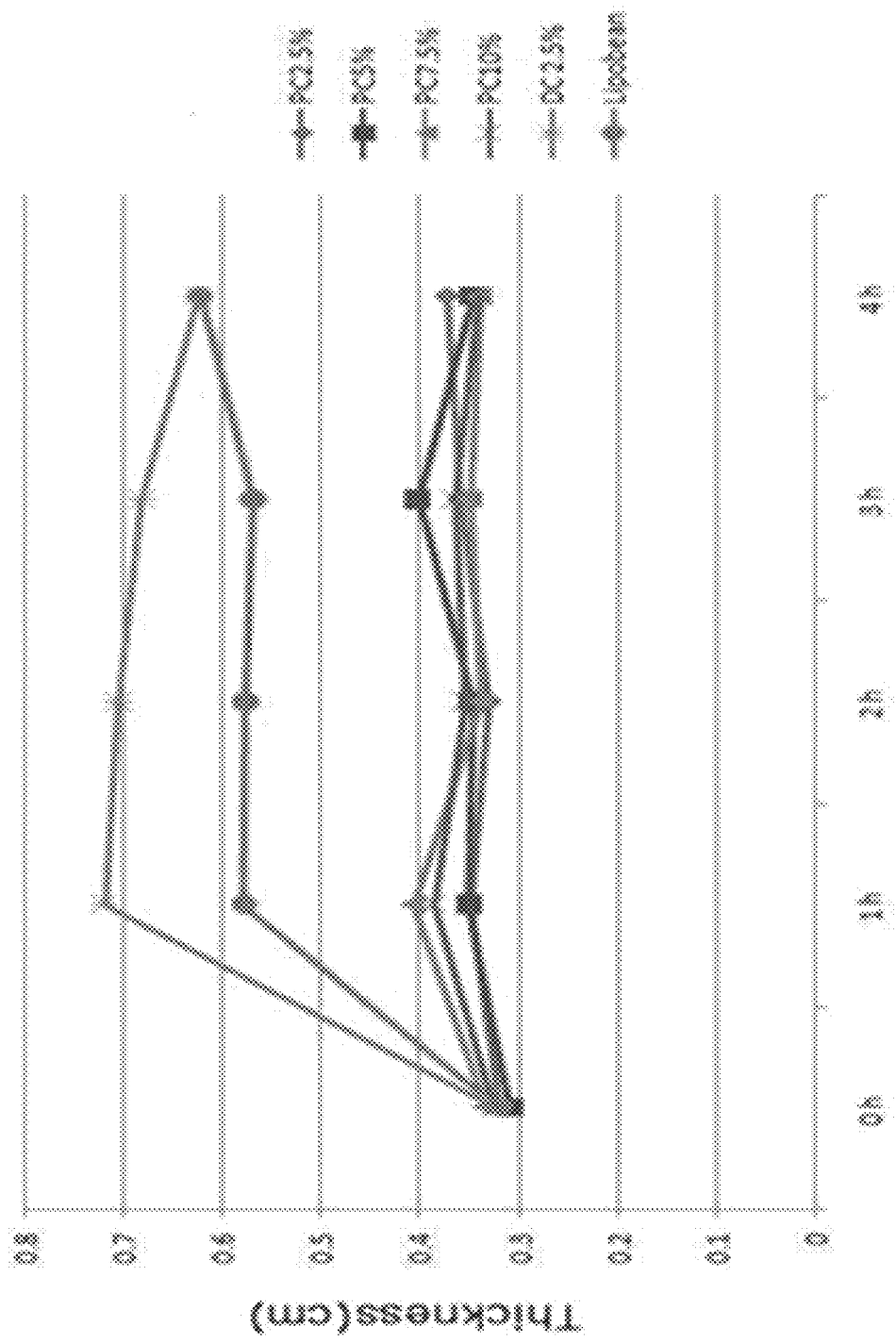
FIG. 1 indicates measurement results showing the thickness of the hind feet of test animals in phosphatidylcholine (PC)-containing injection-administered test groups in its various concentrations and Lipobean-administered control group.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and will not be interpreted in an idealized or overly formal sense, unless expressly so defined herein.

To achieve the above-mentioned object of the present invention, an aspect of the present invention provides a composition for inducing lipolysis comprising 1-15% (w/v) of phosphatidylcholine, 1-30% (w/v) of an oily solvent, and a balance of water. The said % (w/v) is based on the total composition.

Another aspect of the present invention provides a method for inducing a localized lipolysis, the method comprising administering an effective amount of the composition for inducing lipolysis according to the present invention to a subject in need thereof.

Still another aspect of the present invention provides an injectable formulation for inducing lipolysis comprising the composition according to the present invention as an active ingredient.

Still further another aspect of the present invention provides a method for preparing a composition for inducing lipolysis, the method comprising the steps of:

(a) stirring 1-15% (w/v) of phosphatidylcholine at a temperature of 60-80° C. for ½ to 2 hours;

(b) mixing 1-30% (w/v) of an oily solvent, which is heated to 60-80° C., with the stirred mixture of step (a); and (c) adding water until a pre-determined total volume is reached and stirring.

The said % (w/v) is based on the total composition.

The present invention is described in detail as below:

The present invention provides a composition for inducing lipolysis comprising 1-15% (w/v) of phosphatidylcholine, 1-30% (w/v) of an oily solvent, and a balance of water, along with an injectable formulation for inducing lipolysis comprising the composition as an active ingredient.

The composition and the injectable formulation for inducing lipolysis according to the present invention may be applied to a local area of the body which preferably includes, but is not limited to, abdomen, an area beneath chin, forearms, thighs, waists, and buttocks.

The present invention provides a method for inducing a localized lipolysis, the method comprising administering an effective amount of the composition according to the present invention to a subject in need thereof.

In addition, the present invention provides the composition used for inducing lipolysis.

As used herein, the term "effective amount" means an amount by which less inflammatory reaction is induced than positive control group, preferably an amount enough to induce a localized lipolysis without such adverse side effects as edema, erythema, tissue necrosis and inflammation.

As used herein, the term "subject" means an animal, preferably a mammalian animal especially including a human being, while including animal-derived cells, tissues, organs and the like. The subject may be a patient who needs to be treated.

A composition for inducing lipolysis according to the present invention comprises 1-15% (w/v) of phosphatidylcholine, more preferably 2-12% (w/v) of phosphatidylcholine, most preferably 2-18% (w/v) of phosphatidylcholine. Less than 1% (w/v) of phosphatidylcholine does not result in inducing lipolysis, whereas more than 15% (w/v) of phosphatidylcholine may cause severe side-effects such as inflammation, tissue necrosis and edema.

According to one example in which the composition of the present invention prepared into an injectable formulation was tested for its effect on the size of adipocytes and an inflammatory reaction, it was found to be very effective in inducing lipolysis without such side-effects as tissue necrosis and inflammation (See Example 4).

Phosphatidylcholines (essential phospholipids), which are also known as lecithin, as used in the composition of the present invention are the most representative phospholipid, while constituting around 70% of the total phospholipids in egg yolks and around 60% in human serum. Contrary to other lecithin, lecithin of soybeans comprises two fatty acids and linoleic acid.

The composition for inducing lipolysis according to the present invention comprises 1-30% (w/v) of an oily solvent, more preferably 5-12% (w/v) of an oily solvent.

The oily solvent contained in the composition of the present invention means any oily solvent suitable for the preparation of pharmaceutical compositions known in the art. It includes, but is not limited to, vegetable oil, medium-chain triglyceride, cholesterol, and glyceryl stearate. It preferably includes vegetable oil, cholesterol, and glyceryl stearate, while vegetable oil is more preferable. As used herein, vegetable oil is selected from the group consisting of cotton oil, corn oil, sesame seed oil, soybean oil, olive oil, fractionated coconut oil, peanut oil, sunflower seed oil, safflower oil, almond oil, avocado oil, palm oil, palm kernel oil, babassu oil, beechnut oil, linseed oil, rape seed oil, and a combination thereof. Most preferably, it may be soybean oil.

Soybean oil is a (semi)drying oil prepared by solvent extraction from soybean seeds which contain 13-26% of soybean oil. It is utilized in edible oil, margarine and paint. It generally has an iodine value of 125-135, while containing oleic acid as a main component and a trace amount of linoleic acid and palmitic acid.

The above-described composition for inducing lipolysis comprising phosphatidylcholine, an oily solvent and water is disclosed by the present invention for the first time.

Meanwhile, the composition according to the present invention may further comprise at least a substance selected from the group consisting of 0.1-5% (w/v) of an isotonic agent, 0.01-5% (w/v) of a non-ionic surfactant, 0.1-5% (w/v) of a stabilizer and 0.1-5% (w/v) of a preservative.

The isotonic agent as used herein functions to appropriately maintain osmotic pressure when the composition comprising phosphatidylcholine according to the present invention is administered to the body of a subject, while further stabilizing phosphatidylcholine in a solution as its additional effect.

The isotonic agent may be a pharmaceutically acceptable sugar, salt, combination or mixture thereof. For instance, it may include glucose as sugar, while including, as a water-soluble inorganic salt, sodium chloride, calcium chloride, sodium sulfate, glycerin, propylene glycol, polyethylene glycol having a molecular weight of 1,000 or less. More preferably, it may be glycerin. In addition, it may be used as a form of combination of one, two or more said materials. The concentration of isotonic agent is preferably 2-3% (w/v) and may be adjusted properly to ensure that a solution formulation containing each mixture becomes an isotonic solution, depending on the types, amounts and the like of each component in the composition according to the present invention.

The preservative as contained in the composition of the present invention may be selected, but not limited to, from the group consisting of benzyl alcohol, lidocaine, procaine and chlorobutanol. More preferably, it may be benzyl alcohol.

Benzyl alcohol, which is one of aromatic alcohols in a form of colorless, transparent liquid, is utilized as a dissolution agent, an extraction agent, a volatilization suspending agent, and a food flavoring agent due to its peculiar fragrance and a sharp taste. Preferably, the concentration of benzyl alcohol as contained in the composition for inducing lipolysis according to the present invention is 0.1-1% (w/v).

A stabilizer is a material added to improve the stability of phospholipid liposome and may be characterized by being able to be inserted into phospholipids. Such a material includes steroid or steroid-like material, sphingolipid, derivatives thereof, and a combination thereof. Exemplary materials include cholesterol, β-cholesterol, sitosterol, ergosterol, stigmasterol, stigmasterol acetate, lanosterol and combination thereof. Most preferably, it may be cholesterol.

A non-ionic surfactant may be used together with other types of surfactants since it does not produce ions in its state of solution. Non-ionic surfactant which may be used in the composition of the present invention includes, but is not limited to, Tween series surfactant and Poloxamer.

Tween-series surfactant, which is polyoxyethylene sorbitan fatty acid ester, is prepared to improve its hydrophilic property by adding polyoxyethylene substituent to acyl sorbitan. Poloxamer is a non-ionic block copolymer of ethylene oxide and propylene oxide. Poloxamer may be used as a surfactant, an emulsifier, a solubilization agent, or a dispersing agent in the preparation of pharmaceutical formulations.

The composition of the present invention was prepared into an injectable formulation and was tested for its effect on inducing lipolysis.

In one example, the composition for inducing lipolysis according to the present invention was administered to the soles of the hind feet of test mice for visual inspection and histological examination. Compared with positive control groups in which 2.5% sodium deoxycholate alone or in combination with Lipobean were administered, the composition of the present invention did not cause edema and erythema without any finding of neutrophil which is considered as an evidence of inflammatory reaction. MPO Assay, IL-1β ELISA, IL-6 ELISA and PGE2 Assay were performed on mice tissues which were administered with injectable formulations comprising the composition according to the present invention and sodium deoxycholate (DC) as a positive control group, respectively. It was found that, as a whole, the phosphatidylcholine-administered groups showed less inflammatory reaction than the positive control group (See Example 3). Further, when the composition of the present invention was injected into the abdominal subcutaneous fats, it showed not only the effect of lipolysis similar to Lipobean, but also did not cause tissue necrosis or fibrosis in comparison with Lipobean-and DC-administered groups in which severe tissue necrosis with perforation and fibrosis occurred (See Example 4).

When the composition of the present invention is prepared in a form of a pharmaceutical preparation, the active ingredient may be combined with pharmaceutically acceptable and commonly used excipients to prepare into a formulation for oral or parenteral administration according to the purpose of administration. The formulation for oral administration may include, for example, tablets, hard or soft capsules, granules, chewing tablets, pills, powders, elixirs, suspensions, emulsions, solutions, and syrups. The formulation for parenteral administration may include, for example, aerosols, sachets, sterilized injectable solutions and sterilized powders. In addition, an injectable formulation for parenteral administration in a form of solution or emulsion may be parenterally administered, for instance, via subcutaneous, intravenous, intramuscular or intraperitoneal route. In general, injectable solution or emulsion may be prepared by homogeneously mixing an effective amount of an active ingredient within pharmaceutically acceptable liquid excipients such as water, saline water, aqueous dextrose and its related sugar solution, non-volatile oil, ethanol, glycerin, and glycols including polyethylene glycol and propylene glycol.

Besides, if desired, supplementary agents such as an antibacterial agent, a chelating agent, a buffering agent and a preservative may be further included. As used herein, the pharmaceutically acceptable excipients include any supplementary agent which is pharmaceutically pure, substantially non-toxic, and does not inhibit the activity of active ingredients.

An injectable formulation is prepared by dissolving an active ingredient and other additive ingredients in a distilled water for injection, followed by filtration with a bacterial filter and an aseptic processing after which being filled and sealed into vials under aseptic condition. In order to fill up a remaining portion when preparing an injectable formulation, water for injection as well as water may be used. Water for injection may be a distilled water made to dissolve a solid injectable formulation or dilute water-soluble injectable formulation. Exemplary injectable formulation may include glucose injection, xylitol injection, D-mannitol injection, fructose injection, saline water, Dextran 40 injection, Dextran 70 injection, amino acids injection, Ringer's solution, and lactated Ringer's solution.

The present invention provides a method for preparing a composition for inducing lipolysis. The method for preparing a composition for inducing lipolysis according to the present invention is characterized by comprising the steps of:

(a) stirring 1-15% (w/v) of phosphatidylcholine at a temperature of 60-80° C. for ½ to 2 hours;

(b) mixing 1-30% (w/v) of an oily solvent, which is heated to 60-80° C., with the stirred mixture of step (a); and (c) adding water until a pre-determined total volume is reached and stirring.

The method for preparing a composition for inducing lipolysis is described by each step as follows.

(a) stirring 1-15% (w/v) of phosphatidylcholine at a temperature of 60-80° C. for ½ to 2 hours:

In step (a), phosphatidylcholine is added and stirred while being heated to 60-80° C. for ½ to 2 hours. The components and the concentration of phosphatidylcholine in step (a) are the same as described above for the composition of the present invention.

Meanwhile, in step (a), any one or all of 0.1-5% (w/v) of an isotonic agent, 0.01-5% (w/v) of a non-ionic surfactant, 0.1-5% (w/v) of a stabilizer and 0.1-5% (w/v) of a preservative may be further added and stirred. The components and the concentrations of the isotonic agent and the preservative are the same as described above for the composition of the present invention.

(b) mixing 1-30% (w/v) of an oily solvent, which is heated to 60-80° C., with the stirred mixture of step (a):

In step (b), an oily solvent which is heated 60-80° C. is mixed with phosphatidylcholine stirred in step (a). The components and the concentration of an oily solvent is the same as described above for the composition of the present invention.

(c) adding water until a pre-determined total volume is reached and stirring:

Step (c) is to fill with water until the total volume of the composition is reached and stir homogeneously. In this step, an oily solvent and water are mixed together to become a murky solution.

The above described preparation method may comprise a step (d) of miniaturizing the particle size of phosphatidylcholine to range from 10 to 500 nm in diameter through homogenization process with cooling to room temperature. Preferably, the diameter of the particle of phosphatidylcholine is 50-300 nm.

The composition according to the present invention for inducing lipolysis comprising phosphatidylcholine, an oily solvent and water is effective in inducing lipolysis without causing such adverse side effects as edema, erythema, tissue necrosis and inflammation.

Hereinafter, the present invention will be described in detail with reference to following Examples.

However, the following Examples are only for illustrative purposes and are not intended to limit the scope of the present invention.

EXAMPLE 1

Preparation of Phosphatidylcholine-Containing Injectable Composition

Soybean oil (Sigma-Aldrich Company, St. Louis, Mo., USA) as measured on an analytical balance is heated in a water bath of 70±10° C. for 1 hour. At the same time, phosphatidylcholine as a main component, glycerin and benzyl alcohol as measured on an analytical balance were placed into a glass vial in which an appropriate amount of water for injection is added. A magnetic bar is added into the vial, followed by stirring in a stirrer at 800 rpm for 1 hour while heating to 70±10° C. While maintaining the water phase within the vial in the state of stirring at 800 rpm and 70±10° C., the heated an oily is mixed in a drop-by-drop manner. The final volume is set to 10 ml by adding water for injection heated to 70±10° C. Thereafter, while stirring for 5 minutes under the same conditions as described above, it is emulsified in the state of coarse emulsion. The prepared emulsion is cooled to room temperature. The particles of the coarse emulsion are reduced, of which diameter is set to 50-300 nm, by conducting 5 cycles of high pressure homogenizer (Nano DeBEE, B.E.E. International Inc., USA) at 10,000 psi. The phospholipid injectable composition is prepared in the concentrations of 2.5% (w/v), 5%, 7.5% and 10%, respectively.

TABLE 1

Phospholipid injection composition

| Purpose for combination | Name of Substance | Concentration of phospholipid %(w/v) | | | |
|---|---|---|---|---|---|
| | | 2.5 Amount (mg) | 5 Amount (mg) | 7.5 Amount (mg) | 10 Amount (mg) |
| 1 Main ingredient | Phosphatidylcholine | 250.0 | 500.0 | 750.0 | 1000.0 |
| 2 Oily solvent | Soybean oil | 1000.0 | 1000.0 | 1000.0 | 1000.0 |
| 3 Isotonic agent | Glycerin | 225.0 | 225.0 | 225.0 | 225.0 |
| 4 Preservative | Benzyl alcohol | 20.0 | 20.0 | 20.0 | 20.0 |
| 5 Water phase solvent | Water for injection | balance | balance | balance | balance |
| Total | | | 10 ml | | |

EXAMPLE 2

Measurement of Edema and Inflammation

<2-1>Measuring the Size of the Soles of Test Animals 0.1 ml of the injectable compositions of the above Table 1, Lipobean (purchased from Ami Pharm Co., Ltd.; positive control) or 2.5% sodium deoxycholate (hereinafter, "DC"; saline solution was used as a solvent) were injected into the soles of the hind feet of 6 week-old, male Sprague-Dawley rats (weight: 170-200 g), respectively. The thickness of the soles was measured by using calipers at 1, 2, 3, and 4 hours after injection, while test performers were not aware of the order or the purpose of tests (i.e. blind study).

Figure 2:
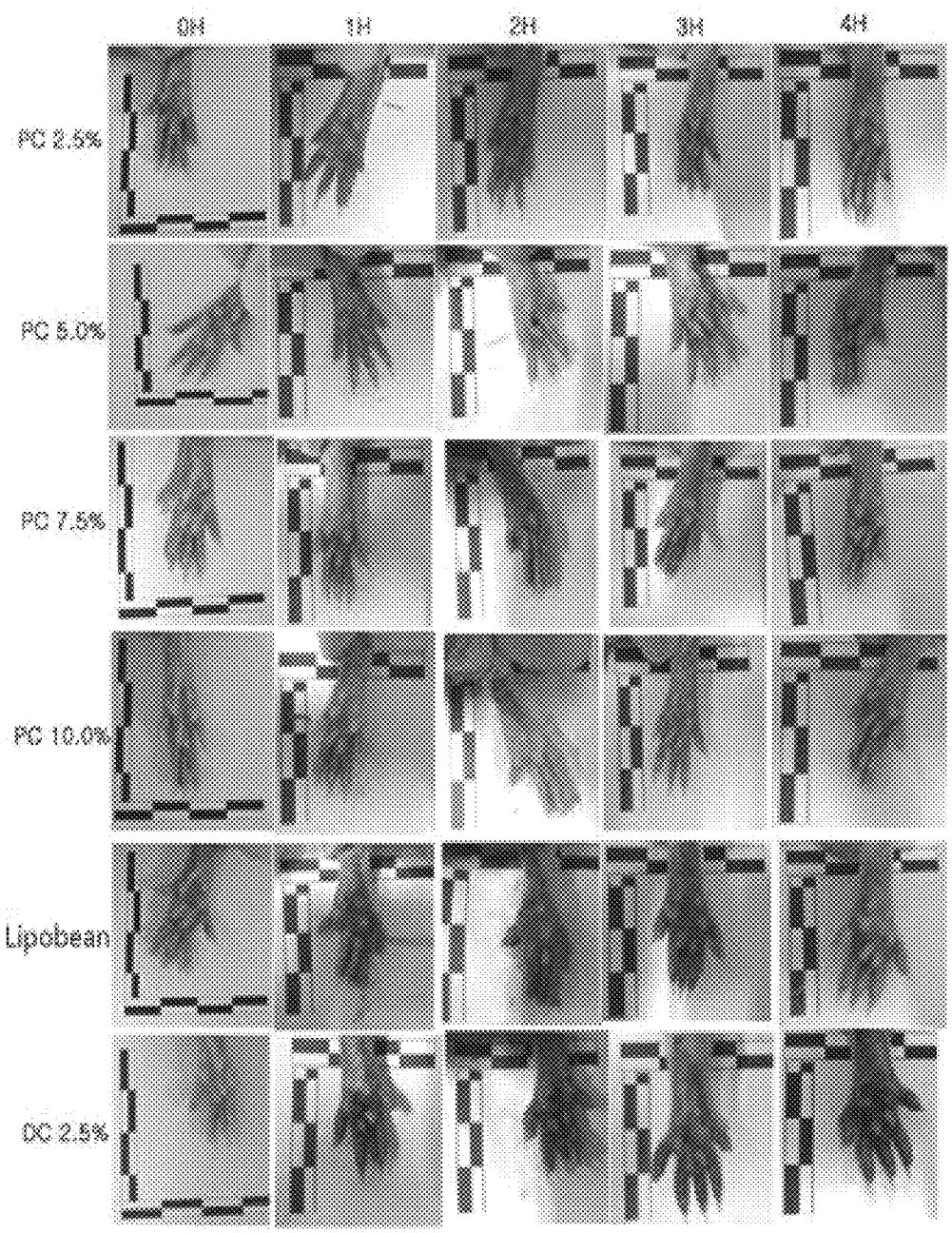
FIG. 2 shows photographs taken over the course of pre-determined time on 4×4cm scale ruler, indicating the shape of the hind feet of test animals in phosphatidylcholine (PC)-containing injection-administered test groups in its various concentrations and Lipobean-administered control group.

The measurement results of thickness are as described in the following Table 2 and FIG. 1, while FIG. 2 shows photographs of the soles taken during the measurement of the thickness of the soles.

TABLE 2

Measurement of the thickness of the feet

| | 0 h | 1 h | 2 h | 3 h | 4 h |
|---|---|---|---|---|---|
| PC 2.5% | 0.321 | 0.350 | 0.332 | 0.360 | 0.373 |
| PC 5% | 0.310 | 0.351 | 0.347 | 0.402 | 0.348 |
| PC 7.5% | 0.335 | 0.408 | 0.339 | 0.351 | 0.341 |
| PC 10% | 0.325 | 0.386 | 0.354 | 0.365 | 0.341 |
| Lipobean | 0.321 | 0.579 | 0.577 | 0.569 | 0.622 |
| DC 2.5% | 0.324 | 0.720 | 0.706 | 0.682 | 0.625 |

As indicated in FIG. 1 and Table 2, the test groups administered with phosphatidylcholine (PC)-containing injectable composition according to the present invention showed significantly thinner hind feet and less erythema than Lipobean- and DC-administered groups, respectively.

<2-2> Histological Tests

Figure 3:
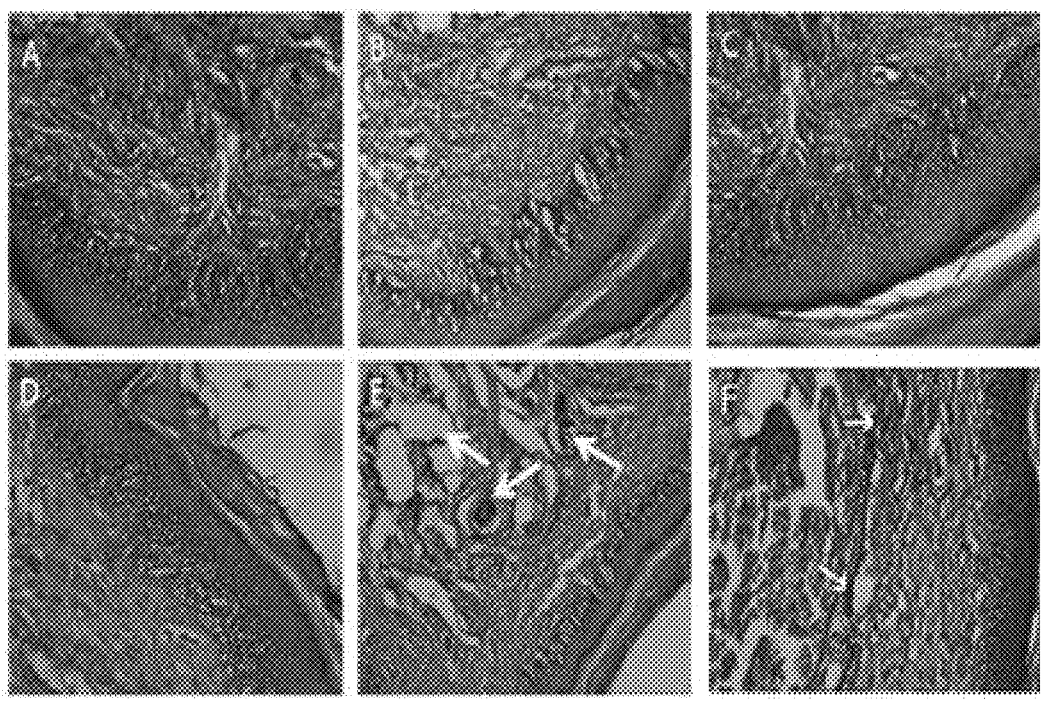
FIG. 3 shows microscopic photographs indicating the tissues of the hind feet of test animals incised and dyed with hematoxylin eosin in phosphatidylcholine (PC)-containing injection-administered test groups in its various concentrations and Lipobean-administered control group (A: 2.5% Phosphatidylcholine (PC)-administered group; B: 5% Phosphatidylcholine (PC)-administered group; C: 7.5% Phosphatidylcholine (PC)-administered group; D: 10% Phosphatidylcholine (PC)-administered group; E: Lipobean-administered group; F: 2.5% Sodium deoxycholate (DC)-administered group; White arrows: Areas in which neutrophils were produced).

Four (4) hours after the above described administration, rats were sacrificed of which soles were removed and their skins were incised and fixated in 10% formalin solution. Then, they were dyed in hematoxylin eosin solution to observe their morphological changes. The results are indicated in FIG. 3.

The test groups administered with phosphatidylcholine (PC)-containing injectable composition according to the present invention showed neither edema nor neutrophils (as indicated with white arrow in FIG. 3), whereas Lipobean- and DC-administered groups showed both edema and neutrophils.

EXAMPLE 3

Effect of Lessening Adverse Side Effects

<3-1> MPO Assay

Myeloperoxidase (MPO) activity was measured by using MPO Activity Colorimetric Assay Kit (BioVision, USA). The tissue samples of the hind feet of test animals in phosphatidylcholine (PC)-containing injection-administered test groups and sodium deoxycholate (DC)-administered group in various concentrations (PC 2.5%, PC 5%, DC 2.5%, PC 5%+DC 2.5%) were mixed in 4 times MPO assay buffer and centrifuged at 12,000 rpm for 10 minutes, followed by diluting each tissue sample with 25 µl of MPO assay buffer, respectively. The diluted samples were placed into standard, background sample of 96-well plate, while dividing reaction mix and background into their corresponding wells and cultivating at 25° C. for 120 minutes. Then, stop mix was added and left for 10 minutes. Subsequently, TNB reagent was added to equalize the total amount of each well to 150 µl, followed by sun blocking with aluminum foils and 10 minutes later measuring absorption value at 412 nm.

Figure 4:
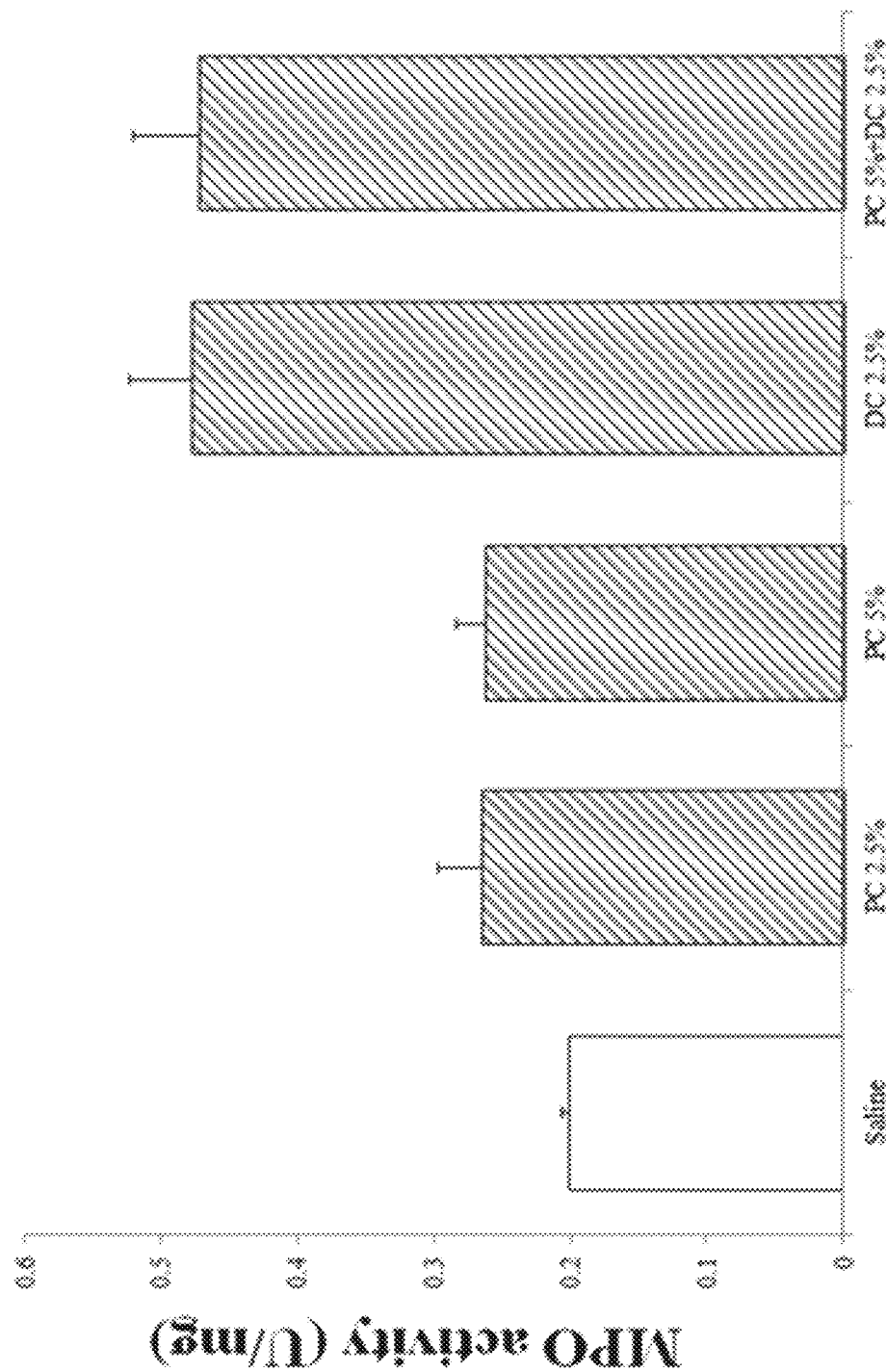
FIG. 4 shows the results of Myeloperoxidase (MPO) Activity Colorimetric Assay on the tissue samples of the hind feet of test animals in phosphatidylcholine (PC)-containing injection-administered test groups in its various concentrations and sodium deoxycholate (DC)-administered positive control group (PC 2.5%: 2.5% Phosphatidylcholine (PC)-administered group; PC 5%: 5% Phosphatidylcholine (PC)-administered group; DC 2.5%: 2.5% Sodium deoxycholate-administered group; PC 5%+DC 2.5%: 5% Phosphatidylcholine (PC) and 2.5% Sodium deoxycholate (DC)-simultaneously administered group).

The results as shown in FIG. 4 indicate that the sodium deoxycholate (DC)-administered group demonstrated an overall higher MPO activity than the present invention's phosphatidylcholine (PC)-containing injection-administered test groups.

<3-2> IL-1β ELISA

IL-1β in test tissue samples was measured with ELISA Kit (Boster Biological Technology Co., Ltd., Fremont, USA). The hind feet tissue samples of test animals in phosphatidylcholine (PC)-containing injection-administered test groups and sodium deoxycholate (DC)-administered group in various concentrations (PC 2.5%, PC 5%, DC 2.5%, PC 5%+DC 2.5%) and biotinylated detection antibodies were placed into wells and cultivated, followed by washing with PBS or TBS buffer. Avidin-Biotin-Peroxidase complex was added and cultivated, followed by washing with PBS or TBS buffer. TMB color developing agent was added, followed by the treatment of TMB stop solution. Within 30 minutes, absorption value of IL-1β was measured at 450 nm.

Figure 5:
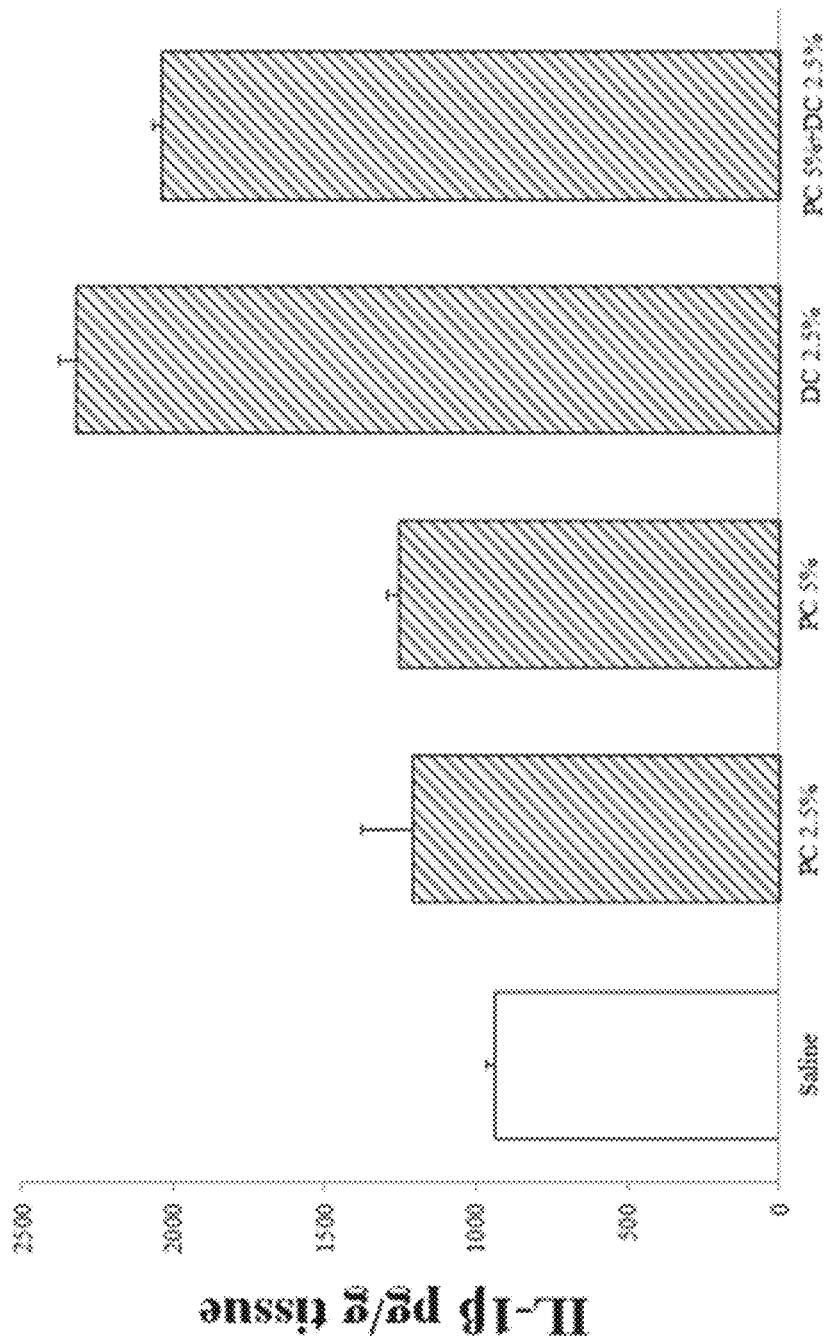
FIG. 5 shows the results of ELISA on IL-1 in the tissue samples of the hind feet of test animals in phosphatidylcholine (PC)-containing injection-administered test groups in its various concentrations and sodium deoxycholate (DC)-administered positive control group (PC 2.5%: 2.5% Phosphatidylcholine (PC)-administered group; PC 5%: 5% Phosphatidylcholine (PC)-administered group; DC 2.5%: 2.5% Sodium deoxycholate-administered group; PC 5%+DC 2.5%: 5% Phosphatidylcholine (PC) and 2.5% Sodium deoxycholate (DC)-simultaneously administered group).

The results as shown in FIG. 5 indicate that phosphatidylcholine (PC)-administered test groups demonstrated less level of IL-1β than the sodium deoxycholate(DC)-administered group, while PC 5%+DC 2.5% group showed less level of IL-1β than DC 2.5% group.

<3-3> IL-6 ELISA

IL-6 in test tissue samples were measured with ELISA Kit (Boster Biological Technology Co., Ltd., Fremont, USA). The hind feet tissue samples of test animals in phosphatidylcholine (PC)-containing injection-administered test groups and sodium deoxycholate (DC)-administered group in various concentrations (PC 2.5%, PC 5%, DC 2.5%, PC 5%+DC 2.5%) and biotinylated detection antibodies were placed into wells and cultivated, followed by washing with PBS or TBS buffer. Avidin-Biotin-Peroxidase complex was added and cultivated, followed by washing with PBS or TBS buffer. TMB color developing agent was added, followed by the treatment of TMB stop solution. Within 30 minutes, absorption value of IL-6 was measured at 450 nm.

Figure 6:
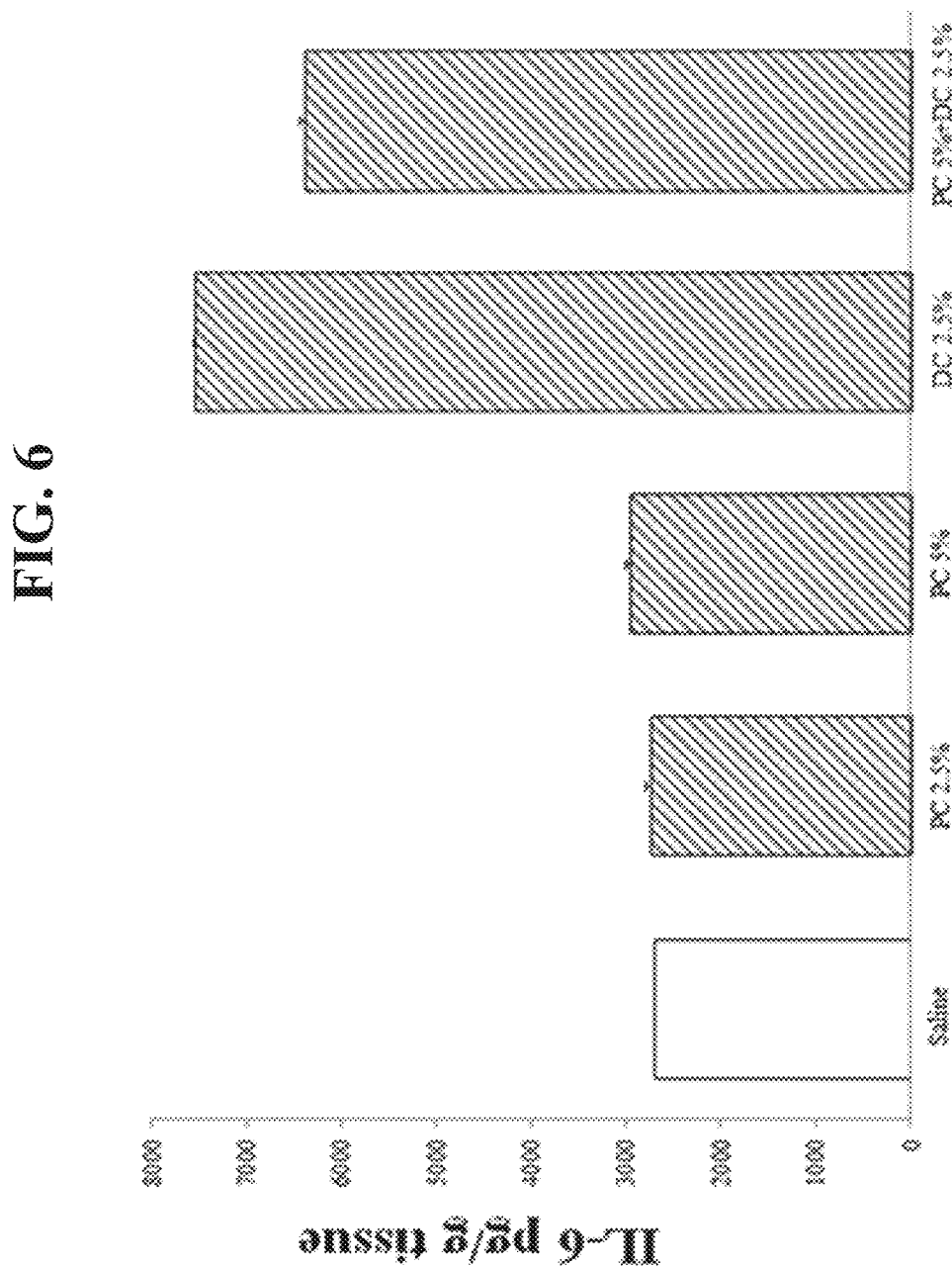
FIG. 6 shows the results of ELISA on IL-6 in the tissue samples of the hind feet of test animals in phosphatidylcholine (PC)-containing injection-administered test groups in its various concentrations and sodium deoxycholate (DC)-administered positive control group (PC 2.5%: 2.5% Phosphatidylcholine (PC)-administered group; PC 5%: 5% Phosphatidylcholine (PC)-administered group; DC 2.5%: 2.5% Sodium deoxycholate-administered group; PC 5%+DC2.5%: 5% Phosphatidylcholine (PC) and 2.5% Sodium deoxycholate (DC)-simultaneously administered group).

The results as shown in FIG. 6 indicate that phosphatidylcholine (PC)-administered test groups demonstrated less level of IL-6 than the sodium deoxycholate (DC)-administered group, while PC 5%+DC 2.5% group showed less level of IL-6 than DC 2.5% group.

<3-4> PGE2 Assay

Prostaglandin E2 (PGE2) in the hind feet tissue samples of test animals in phosphatidylcholine (PC)-containing injection-administered test groups and sodium deoxycholate (DC)-administered group in various concentrations (PC 2.5%, PC 5%, DC 2.5%, PC 5%+DC 2.5%) was measured with PGE2 Assay (R&D System Inc., Minneapolis, USA). During cultivation, PGE2s in the hind feet tissue samples bound competitively with horse radish peroxidase (HRP)-labeled PGE2 to their mouse monoclonal antibodies. Unbound materials were removed by using washing buffer, while substrate solution was added to each well and left at room temperature with sunlight blocked. Then, stop solution was added, followed by measuring absorption value at 450 nm.

Figure 7:
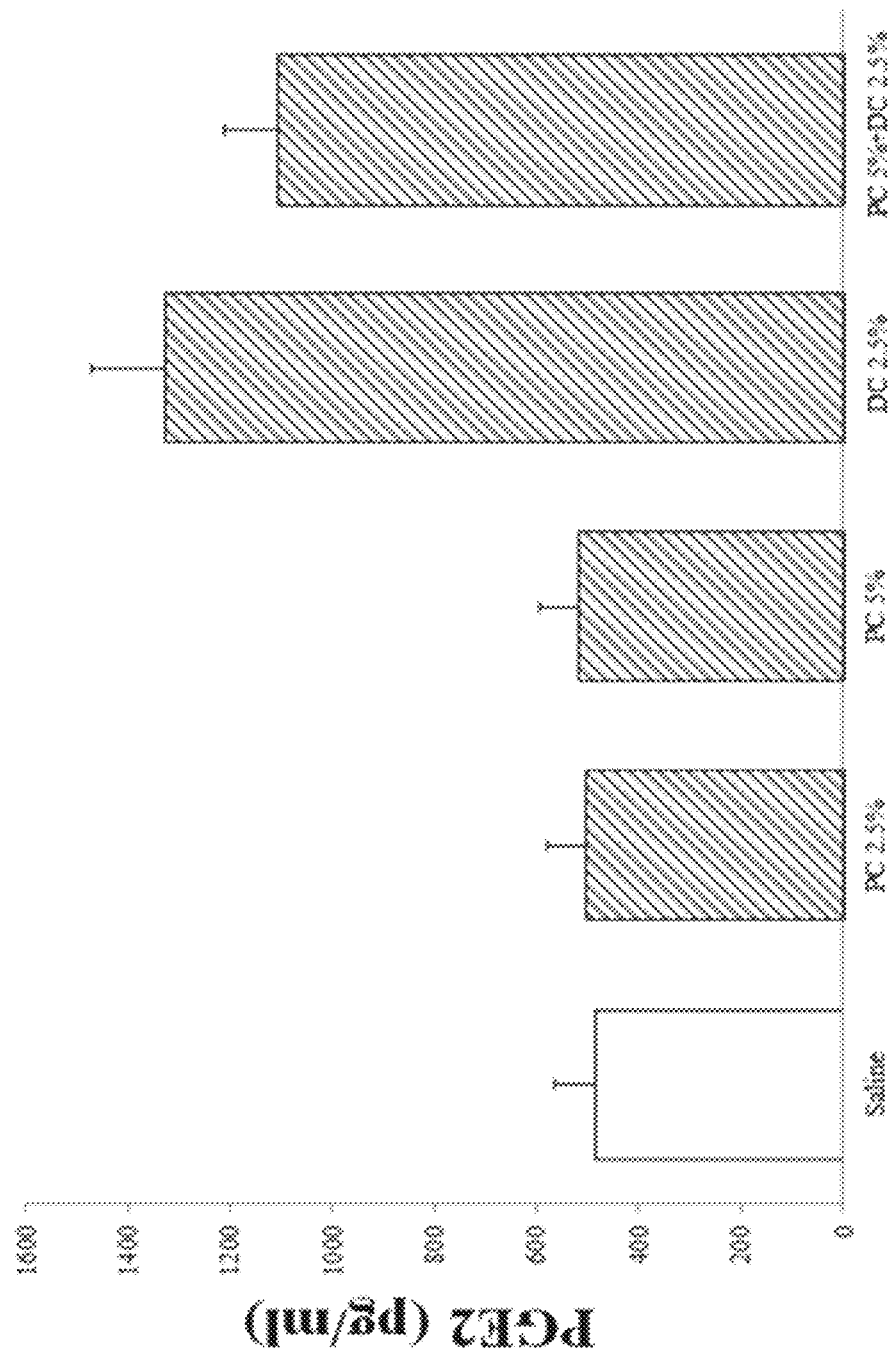
FIG. 7 shows the results of PGE2 Assay on prostaglandin E2 (PGE2) in the tissue samples of the hind feet of test animals in phosphatidylcholine (PC)-containing injection-administered test groups in its various concentrations and sodium deoxycholate (DC)-administered positive control group (PC 2.5%: 2.5% Phosphatidylcholine (PC)-administered group; PC 5%: 5% Phosphatidylcholine (PC)-administered group; DC 2.5%: 2.5% Sodium deoxycholate-administered group; PC 5%+DC 2.5%: 5% Phosphatidylcholine (PC) and 2.5% Sodium deoxycholate (DC)-simultaneously administered group).

The results as shown in FIG. 7 indicate that the sodium deoxycholate (DC)-administered group demonstrated two (2) or more times higher level of PGE2 than phosphatidylcholine (PC)-administered test groups, while PC 5%+DC 2.5% group showed less level of PGE2 than DC 2.5% group.

EXAMPLE 4

Effect of Tissue Necrosis and Lypolysis

<4-1> Experiment Preparation

Albino C57BL/6 mice (4 weeks old) were fed with high fat diet (Research diet, 60% kcal lipid) to induce a high degree of obesity. Then, after 24 and 48 hours, 0.2 ml of saline solution (negative control group), injection compositions of Table 1, Lipobean, 2.5% DC were injected subcutaneously into the abdomen of the mice, respectively. Eight (8) days after the administration was completed, the mice were sacrificed.

<4-2> Determination of Tissue Necrosis Through Visual Inspection

Figure 8:
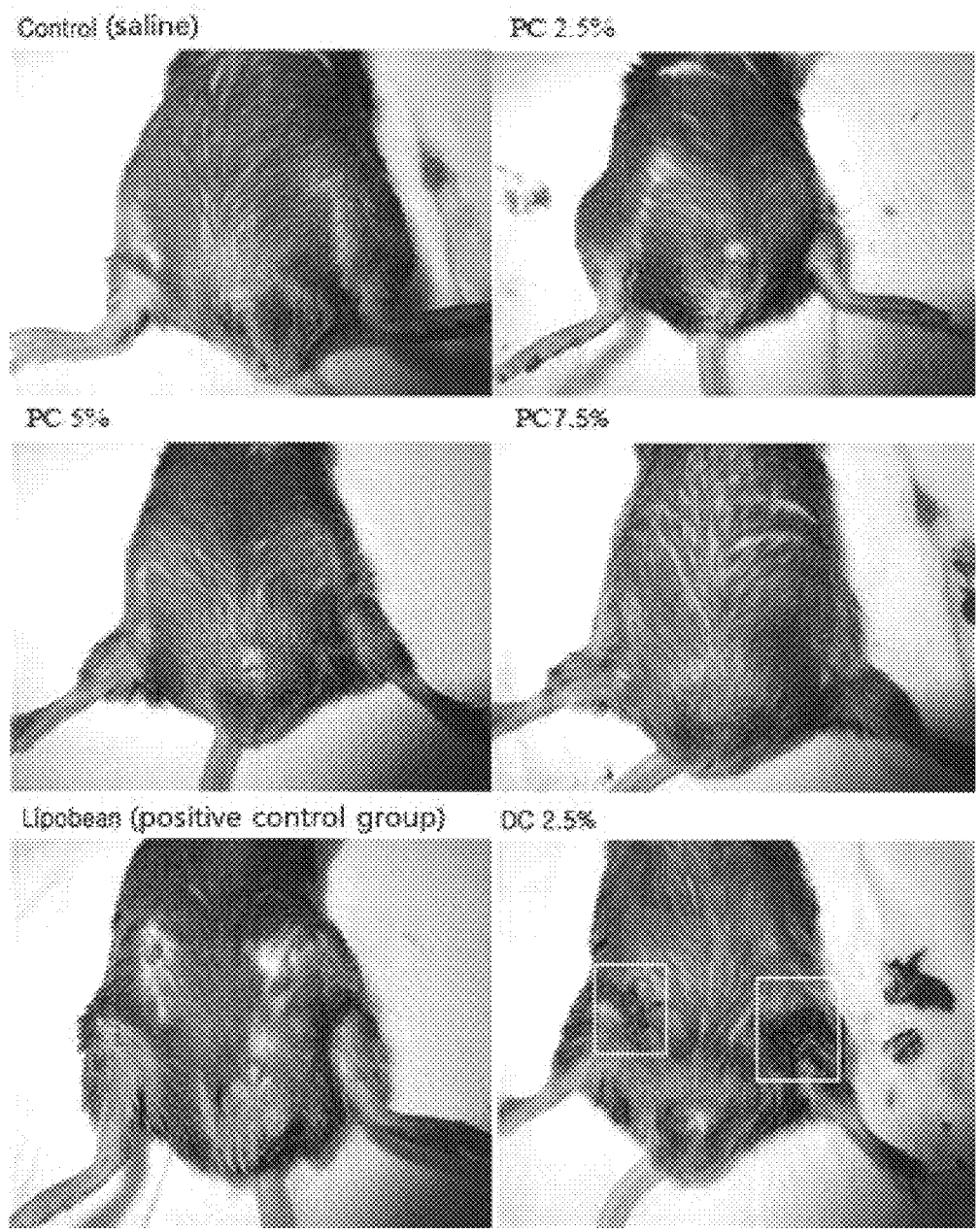
FIG. 8 shows photographs of the abdominal areas of the sacrificed test animals in phosphatidylcholine (PC)-containing injection-administered test groups in its various concentrations and control group.

Visual inspection was conducted on the subcutaneously injected areas of the sacrificed mice. The results are presented in FIG. 8. In the phosphatidylcholine-injected test groups, no necrosis or mass was detected via visual inspection, while the injected areas did not feel hard upon touching. On the contrary, the Lipobean-administered group showed necrosis around the injected area with a significantly hard feeling upon touching. In the 2.5% DC-administered group, there was severe necrosis with perforation in the skin, while fibrosis was spread to the surrounding tissues as detected by autopsy (photographs not shown).

<4-3> Observation of Adipocytes

The abdomen of the sacrificed mice was incised, followed by rapid extraction of subcutaneous fats and their fixation in 4% formaldehyde solution. After fixation, washing & dehydrating were conducted and treated with paraffin solution to prepare paraffin blocks. Then, those paraffin blocks were thin-sliced in the thickness of 4 μm which were then dyed with hematoxylin & eosin for an optical microscopic observation. The results are shown in FIG. 9.

Figure 9:
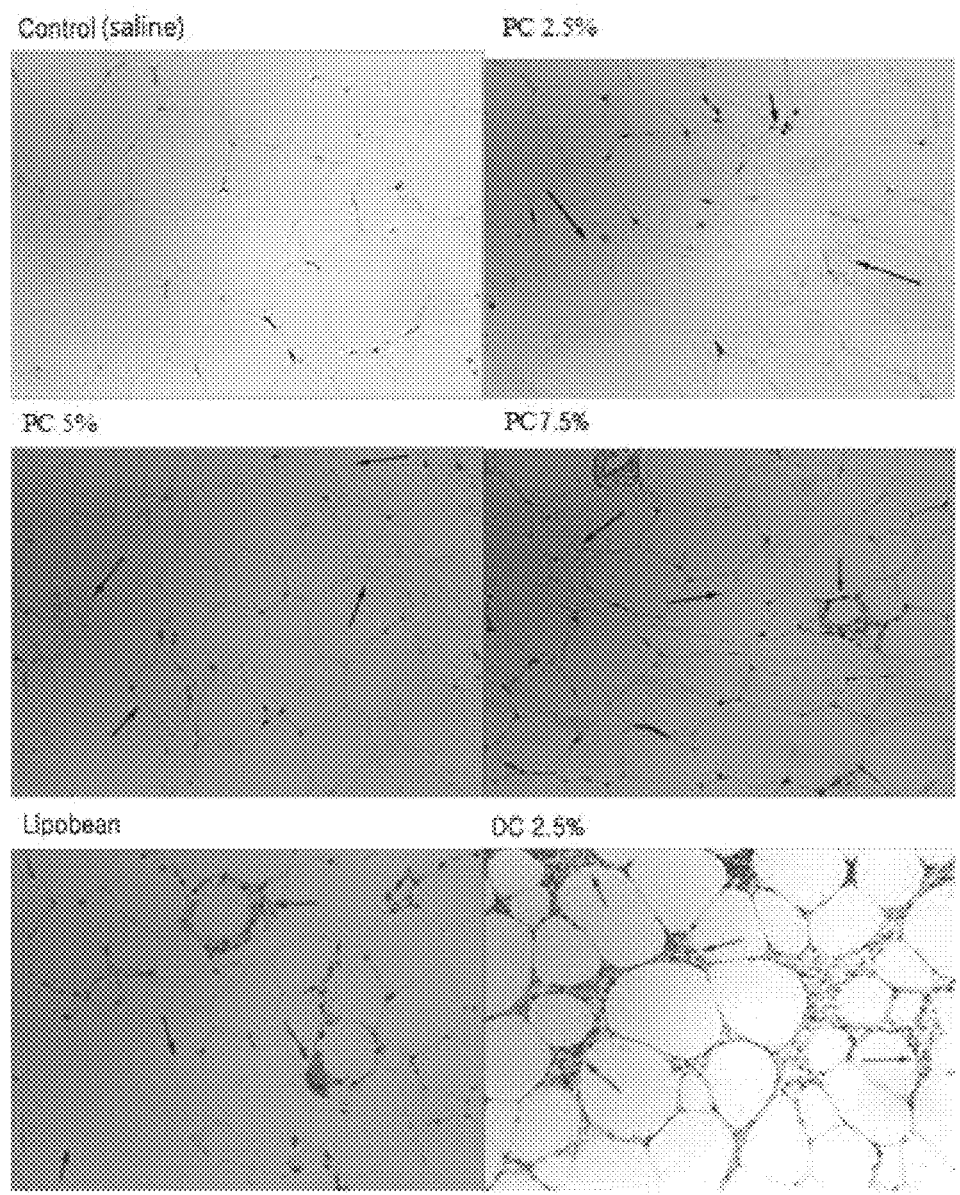
FIG. 9 shows optical microscopic photographs of H&E dyed-abdominal subcutaneous fatty tissues from the sacrificed test animals in phosphatidylcholine (PC)-containing injection-administered test groups in its various concentrations and control group (Dark arrows: Areas of lipolysis; Red arrows: Areas of inflammation).

As seen in FIG. 9, the 2.5% phosphatidylcholine (PC)-administered test group showed intact adipocytes which were almost the same as those in saline control group, while some adipose tissues were dissolved (as shown with black arrow). In comparison with the saline control group, the 5% phosphatidylcholine (PC)-containing injection-administered test group showed traces of lipolysis in multiple areas, with a greater level of lipolysis compared with the 2.5% PC-administered group. In the 7.5% PC-administered group, it was found that granulocytes were gathered to cause a mild inflammatory reaction (as shown with red arrows), as well as traces of lipolysis. The Lipobean-administered group showed a similar level of lipolysis to the 5% PC-administered group, with a slight inflammation. Almost no lipolysis effect was detected in the 2.5% DC-administered group, while showing a greater degree of inflammation than other groups.

The size of adipocytes in the saline control group and the PC injection-administered group were measured. The results are described in the following Table 3.

TABLE 3

| | The size of adipocytes | | | |
|---|---|---|---|---|
| | Saline control | PC 2.5% | PC 5.0% | PC 7.5% |
| Size | 116.7 ± 8.9 | 102.7 ± 5.9 | 91.9 ± 10.4 | 95.8 ± 15.2 |

As a whole, it was found that the size of adipocytes was decreased in a phosphatidylcholine concentration dependent manner. However, it was noticeable that PC 5.0% group showed the best effect in comparison with PC 7.5% group. This result suggests that the occurrence of inflammation in PC 7.5% group might have affected its effect of lipolysis.

Preparation Example 1

Preparation of Cholesterol (Stabilizer)-Containing Injection Composition

10% (w/v, based on the total composition) phosphatidylcholine and 2% (w/v) cholesterol are completely dissolved in an organic solvent, i.e. ethanol in a round bottom flask. Ethanol is evaporated at 70° C. or less by using a reduced pressure distillation apparatus, thereby drying phosphatidylcholine. Tween-series surfactant (1% (w/v) based on the total composition) is added to an appropriate amount of a distilled water, and then the resulting mixture is added to the dried phosphatidylcholine to form crude liposomes. The crude liposomes are adjusted by using a homogenizer to have their particle diameter of 10-500 nm. Cholesterol functions to enhance the stability of phosphatidylcholine particles.

Preparation Example 2

Preparation of Injectable Composition Using Glyceryl Stearate (Oily Solvent)

Glyceryl stearate (10% (w/v)) is dissolved at 60° C., and 5% (w/v) poloxamer and 5% (w/v) phosphatidylcholine are added thereto. The mixture is cooled to room temperate (20° C.) while being homogenized by a homogenizer. Then, an appropriate amount of a distilled water is added and homogenized to render the particle diameter in the range of 10-500 nm. The amount of each said component is described based on the total composition.

The composition comprising phosphatidylcholine, an oily solvent and water in accordance with the present invention is effective in inducing lipolysis and does not cause such adverse side effects as edema, tissue necrosis and inflammation. Thus, the composition of the present invention may be used as an agent for inducing lipolysis with less adverse side effects, thereby possessing a great industrial applicability.

Although certain exemplary embodiments and implementations have been described herein, other embodiments and modifications will be apparent from this description. Accordingly, the inventive concept is not limited to such embodiments, but rather to the broader scope of the presented claims and various obvious modifications and equivalent arrangements.

What is claimed is:

1. An injectable composition for inducing lipolysis, comprising:
   1-15% (w/v) of phosphatidylcholine,
   1-30% (w/v) of an oily solvent,
   0.1-5% (w/v) of an isotonic agent,
   0.1-5% (w/v) of a preservative selected from the group consisting of benzyl alcohol, lidocaine, procaine and chlorobutanol, and
   a balance of water,
   wherein the oily solvent is a vegetable oil.

2. The composition of claim 1, wherein the composition comprises 2-12% (w/v) of phosphatidylcholine.

3. The composition of claim 1, wherein the composition further comprises at least one substance selected from the group consisting of 0.01-5% (w/v) of a non-ionic surfactant and 0.1-5% (w/v) of a stabilizer.

4. A method for inducing a localized lipolysis, the method comprising administering an effective amount of the composition of claim 1 to a subject in need thereof.

* * * * *